US012765781B2

(12) United States Patent
Marine et al.

(10) Patent No.: US 12,765,781 B2
(45) **Date of Patent: *Oct. 20, 2026**

(54) SYSTEM, METHOD, AND APPARATUS FOR TEMPERATURE ASYMMETRY MEASUREMENT OF BODY PARTS

(71) Applicant: UAB Diabetis, Vilnius (LT)

(72) Inventors: Gintare Marine, Vilnius (LT); Urte Steikuniene, Vilnius (LT); Jonas Guzaitis, Kaunas (LT); Rytis Zajanckauskas, Vilnius (LT)

(73) Assignee: UAB Diabetis, Vilnius (LT)

( * ) Notice: Subject to any disclaimer, the term of this patent is extended or adjusted under 35 U.S.C. 154(b) by 0 days.

This patent is subject to a terminal disclaimer.

(21) Appl. No.: 19/247,244

(22) Filed: Jun. 24, 2025

(65) Prior Publication Data

US 2025/0318733 A1 Oct. 16, 2025

Related U.S. Application Data

(63) Continuation of application No. 18/583,834, filed on Feb. 21, 2024, now Pat. No. 12,364,396, which is a continuation of application No. 17/155,647, filed on Jan. 22, 2021, now Pat. No. 11,950,883, which is a continuation-in-part of application No. 16/646,103, filed as application No. PCT/IB2020/051950 on Mar. 6, 2020, now Pat. No. 12,544,003.

(51) Int. Cl.

| | |
|---|---|
| ***A61B 5/00*** | (2006.01) |
| ***A61B 5/01*** | (2006.01) |

(52) U.S. Cl.

CPC ............ *A61B 5/015* (2013.01); *A61B 5/0013* (2013.01); *A61B 5/0035* (2013.01); *A61B 5/0075* (2013.01); *A61B 5/0077* (2013.01); *A61B 5/6898* (2013.01); *A61B 5/702* (2013.01); *A61B 5/7282* (2013.01); *A61B 5/7475* (2013.01); *A61B 2576/00* (2013.01)

(58) Field of Classification Search

CPC ..... A61B 5/015; A61B 5/0013; A61B 5/0035; A61B 5/0075; A61B 5/0077; A61B 5/6898; A61B 5/702; A61B 5/7282; A61B 5/7475; A61B 2576/00

See application file for complete search history.

(56) References Cited

U.S. PATENT DOCUMENTS

| | | | | |
|---|---|---|---|---|
| 11,950,883 B2 * | 4/2024 | Marine | .................. | A61B 5/015 |
| 12,364,396 B2 * | 7/2025 | Marine | ................ | A61B 5/6898 |

* cited by examiner

*Primary Examiner* — Joel Lamprecht

(57) ABSTRACT

Systems, methods, and apparatus for identifying a health disorder based on a temperature asymmetry estimation. A system may include a thermal camera configured to detect thermal images of an inspected body part and a reference body part, which may be contralateral to the inspected body part. The system may further include an optical camera configured to detect optical images of the inspected body part and the reference body part. The system may further include a remote mobile device having a mobile processor programmed to control the thermal camera to detect the thermal images and the optical camera to detect the optical images. The system may further include remote server having a diagnostic processor programmed to determine that a functional disorder or inflammation of the inspected body part has occurred by analyzing the thermal images and the optical images.

20 Claims, 6 Drawing Sheets

SYSTEM, METHOD, AND APPARATUS FOR TEMPERATURE ASYMMETRY MEASUREMENT OF BODY PARTS

CROSS REFERENCE TO RELATED APPLICATIONS

This application is a continuation of U.S. application Ser. No. 18/583,834, titled System, Method, And Apparatus For Temperature Asymmetry Measurement Of Body Parts and filed on Feb. 21, 2024, which is a continuation of U.S. Application Ser. No. 17/155,647, titled System, Method, And Apparatus For Temperature Asymmetry Measurement Of Body Parts and filed on Jan. 22, 2021, which is a continuation-in-part of U.S. application Ser. No. 16/646,103, titled System, Method, And Apparatus For Temperature Asymmetry Measurement Of Body Parts and filed on Mar. 10, 2020, which is a National Stage Entry of PCT/IB2020/051950, titled System, Method, And Apparatus For Temperature Asymmetry Measurement Of Body Parts and filed on Mar. 6, 2020. The entire contents of all referenced applications are hereby incorporated by reference in their entirety.

BACKGROUND

1. Field

The present disclosure relates to systems, methods, and apparatus for thermal imaging in medical applications and, more particularly, to temperature asymmetry estimation of body parts.

2. Description of the Related Art

Generally, one's body temperature is higher than the ambient temperature. Certain techniques, such as infrared thermal imaging, enable temperature maps of human body or other animal body parts to be produced. When a person experiences a disease or a functional change affecting a body part, temperature of the affected body part may be significantly different compared to that of normal tissue. Inflammation, pre-cancerous tissue formation, tumor growths, and other factors may increase affected body part temperature, while diseases such as vasculitis or artery sclerosis may decrease affected body part temperature.

For example, diabetic foot wounds, or diabetic foot ulcers (DFUs) are among the most common foot complications, critically affecting approximately 15% of the diabetic population. Causes of risk that may lead to the development of foot ulcers are primarily neuropathy and arterial disease in the lower limbs. For diabetic persons with neuropathy, DFUs may develop after minor wounds or skin lesions on the lower limb. DFUs are difficult to diagnose early, and even more difficult to treat. Delayed diagnosis, treatment, and other factors may contribute to further complications of the ulcer, which often lead to the need for surgical interventions and, in some cases, even amputations. Generally, evaluation of DFU requires a multidisciplinary foot care team. Such evaluation may include the medical history of the person, laboratory test results, and dermatological, musculoskeletal, neurological, and vascular status. Self-inspection of one's feet is an important part of detecting diabetic complications in early stages, but this is often impeded by health impairments related to diabetes and other comorbidities, such as eyesight, limited mobility, and social impairments. An alternative to self-evaluation is frequent examination by healthcare professionals, but this is generally costly, time-consuming, and not a common option for many people.

Thus, an advanced self-assessment tool to monitor the feet of people with diabetes is needed.

Described herein are systems, methods, and apparatus for identifying a health disorder based on a temperature asymmetry estimation. A system may have a thermal camera. The thermal camera may be configured to detect thermal images. The system may further have an optical camera. The optical camera may be configured to detect optical images of an inspected body part and a reference body part. The reference body part may be contralateral to the inspected body part. The system may further have a processor to determine that a functional disorder or inflammation of the inspected body part has occurred by analyzing the thermal images and the optical images.

In accordance with an embodiment of the present disclosure, there may be a system for identifying a health disorder based on a temperature asymmetry estimation. The system may have an imaging device. The imaging device may have a thermal camera. The thermal camera may be configured to detect thermal images corresponding to an inspected body part and a reference or contralateral body part. The imaging device may have an input/output port. The imaging input/output port may be configured to transmit the thermal images and the optical images. The system may have an optical camera. The optical camera may be configured to detect optical images corresponding to the inspected body part and the reference or contralateral body part. The system may further have a diagnostic processor. The diagnostic processor may be remote from the imaging device. The diagnostic processor may be programmed to determine that a functional disorder or inflammation of the inspected body part has occurred by analyzing the thermal images and the optical images.

The system may further have a mobile device. The mobile device may be remote from the imaging device. The mobile device may have an input device. The input device may be configured to receive user input corresponding to a request to begin image capture. The mobile device may further have a mobile processor. The mobile processor may be programmed to control the thermal camera and the optical camera to detect the thermal images and the optical images, respectively, based on the received user input.

The system may further have a remote server. The remote server may have the diagnostic processor and a server input/output port. The mobile device may further have a mobile input/output port configured to receive the thermal images and the optical images from the imaging input/output port. The mobile processor may be further programmed to control the mobile input/output port to transmit the thermal images and the optical images to the server input/output port.

The diagnostic processor may be further configured to estimate an inspected recorded image displacement based on an inspected optical image of the optical images and an inspected thermal image of the thermal images. The inspected optical image and the inspected thermal image may correspond to the inspected body part. The diagnostic processor may be further configured to estimate a reference recorded image displacement based on a reference optical image of the optical images and a reference thermal image of the thermal images. The reference optical image and the reference thermal image may correspond to the reference or contralateral body part. Determining that the functional disorder or inflammation of the inspected body part has occurred may be performed by comparing the inspected thermal image to the reference thermal image based on the inspected recorded image displacement corresponding to the inspected body part and the reference recorded image displacement corresponding to the reference or contralateral body part. The mobile input/output port may be configured to be physically and logically coupled to the imaging input/output port of the imaging device. The optical camera may be located on the mobile device such that the physical coupling of the mobile input/output port to the imaging input/output port maintains a constant positioning of the optical camera relative to the thermal camera. The optical camera may be located on the imaging device.

The system may further have a base unit. The base unit may have a support rest. The support rest may be configured to receive and support the inspected body part and the reference or contralateral body part. The base unit may have an imaging connector. The imaging connector may be configured to be physically coupled to the imaging device and to retain the imaging device in place relative to the support rest. The inspected body part may have a first leg or foot. The reference or contralateral body part may have a second leg or foot. The support rest may have a first physical support. The first physical support may be configured to receive and support the first leg or foot. The support rest may have a second physical support. The second physical support may be configured to receive and support the second leg or foot. The base unit may have a body portion having the support rest. The base unit may further have a device portion having the imaging connector. The base unit may further have an extendable portion between the body portion and the device portion. The extendable portion may be configured to at least one of extend or contract to adjust a distance between the support rest and the imaging connector. The system may further have an output device coupled to the diagnostic processor. The output device may be configured to output status data corresponding to a current status of the imaging device.

In accordance with an aspect of the current disclosure, there may be a system for identifying a health disorder based on a temperature asymmetry estimation. The system may have an imaging device. The imaging device may have a thermal camera. The thermal camera may be configured to detect thermal images corresponding to an inspected body part and a reference or contralateral body part. The imaging device may further have an optical camera. The optical camera may be configured to detect optical images corresponding to the inspected body part and the reference or contralateral body part. The imaging device may have an imaging input/output port. The imaging input/output port may be configured to transmit the thermal images and the optical images. The system may further have a diagnostic processor. The diagnostic processor may be remote from the imaging device. The diagnostic processor may be programmed to determine that a functional disorder or inflammation of the inspected body part has occurred by analyzing the thermal images and the optical images.

The system may further have a mobile device. The mobile device may be remote from the imaging device. The mobile device may have an input device. The input device may be configured to receive user input corresponding to a request to begin image capture. The mobile device may have a mobile processor. The mobile processor may be programmed to control the thermal camera and the optical camera to detect the thermal images and the optical images, respectively, based on the received user input. The system may further include a remote server. The remote server may have the diagnostic processor and a server input/output port. The mobile device may further have a mobile input/output port. The mobile input/output port may be configured to receive the thermal images and the optical images from the imaging input/output port. The mobile processor may be further programmed to control the mobile input/output port to transmit the thermal images and the optical images to the server input/output port.

The diagnostic processor may be further configured to estimate an inspected recorded image displacement based on an inspected optical image of the optical images and an inspected thermal image of the thermal images. The inspected optical image and the inspected thermal image may correspond to the inspected body part. The diagnostic processor may be further configured to estimate a reference recorded image displacement based on a reference optical image of the optical images and a reference thermal image of the thermal images. The reference optical image and the reference thermal image may correspond to the reference or contralateral body part. Determining that the functional disorder or inflammation of the inspected body part has occurred may be performed by comparing the inspected thermal image to the reference thermal image based on the inspected recorded image displacement corresponding to the inspected body part and the reference recorded image displacement corresponding to the reference or contralateral body part.

The system may further have a base unit. The base unit may have a support rest. The support rest may be configured to receive and support the inspected body part and the reference or contralateral body part. The base unit may have an imaging connector. The imaging connector may be configured to be physically coupled to the imaging device and to retain the imaging device in place relative to the support rest.

In accordance with an aspect of the present disclosure, there may be a method for identifying a health disorder based on a temperature asymmetry estimation. The method may include detecting thermal images corresponding to an inspected body part and a reference or contralateral body part with a thermal camera of an imaging device. The method may further include detecting optical images corresponding to the inspected body part and the reference or contralateral body part with an optical camera of the imaging device. The method may further include receiving the thermal images and the optical images by a mobile device. The method may further include transmitting the thermal images and the optical images to a server by the mobile device. The method may further include determining that a functional disorder or inflammation of the inspected body part has occurred by analyzing the thermal images and the optical images with a diagnostic processor of the server. The method may further include receiving user input corresponding to a request to begin image capture with an input device of the mobile device. The method may further include controlling the thermal camera and the optical camera to detect the thermal images and the optical images, respectively, based on the received user input with a mobile processor of the mobile device.

The method may further include estimating an inspected recorded image displacement based on an inspected optical image of the optical images and an inspected thermal image of the thermal images with the diagnostic processor. The inspected optical image and the inspected thermal image may correspond to the inspected body part. The method may further include estimating a reference recorded image displacement based on a reference optical image of the optical images and a reference thermal image of the thermal images with the diagnostic processor. The reference optical image and the reference thermal image may correspond to the reference or contralateral body part. Determining that the functional disorder or inflammation of the inspected body part has occurred may be performed by comparing the inspected thermal image to the reference thermal image based on the inspected recorded image displacement corresponding to the inspected body part and the reference recorded image displacement corresponding to the reference or contralateral body part. The method may further include outputting status data corresponding to a current status of the imaging device with an output device.

BRIEF DESCRIPTION OF THE DRAWINGS

Other systems, methods, features, and advantages of the present invention will be or will become apparent to one of ordinary skill in the art upon examination of the following figures and detailed description. It is intended that all such additional systems, methods, features, and advantages be included within this description, be within the scope of the present invention, and be protected by the accompanying claims. Component parts shown in the drawings are not necessarily to scale and may be exaggerated to better illustrate the important features of the present invention. In the drawings, like reference numerals designate like parts throughout the different views, wherein:

DETAILED DESCRIPTION

The systems, methods, and apparatus described herein identify a health disorder based on a temperature asymmetry estimation. The identified health disorder may be a functional disorder or an inflammation. Particularly, the identified health disorder may be a diabetic foot wound, or a diabetic foot ulcer (DFU). The systems may capture thermal images of an inspected body part and a reference body part of a person via a thermal camera. The systems may further capture optical images of the inspected body part and the reference body via an optical camera. The inspected body part may be a foot or a leg of the person. The reference body part may be a contralateral foot or leg of the person. The thermal and optical cameras may be controlled by a mobile device. The thermal and optical images may be transmitted to a remote processor, which may be a processor of a remote server. The processor may analyze the thermal and optical images and advantageously determine that the inspected body is experiencing a functional disorder or an inflammation. More specifically, the processor may estimate a recorded image displacement of the inspected body part and a recorded image displacement of the reference body part and compare the two estimates to make the determination that the body part is experiencing a health disorder. The estimation of the recorded image displacement of the inspected body part may be based on the optical image and thermal image of the inspected body part. The estimation of the recorded image displacement of the reference body part may be based on the optical image and thermal image of the reference body part. The systems may have an output device in communication with the processor to advantageously output data indicating that the body part is experiencing a health disorder. Tests conducted using the systems may be self-administered. The systems may be advantageously used without requiring the help of another person or a healthcare professional. Alternately, the systems are advantageously suitable for use with the assistance of another person or a healthcare professional if needed. As such, "user" may refer to a patient, a healthcare professional, a guardian, a helper, or a caregiver.

Figure 1:
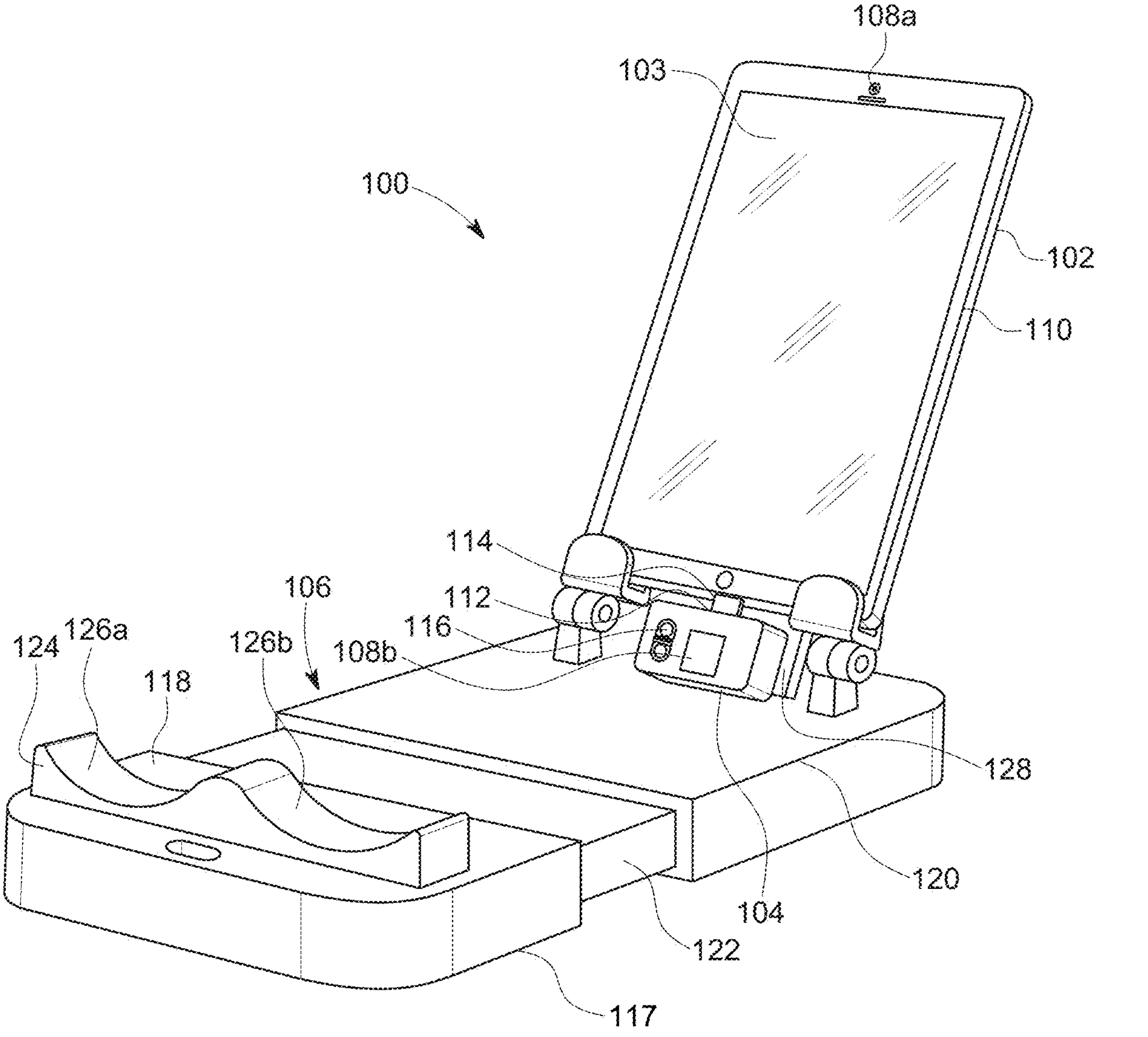
FIG. 1 illustrates a perspective view of a system for identifying a health disorder based on a temperature asymmetry estimation according to an aspect of the present disclosure.

FIG. 1 illustrates a perspective view of a system 100 for identifying a health disorder based on a temperature asymmetry estimation according to an aspect of the present disclosure. The system 100 may have a mobile device 102, an imaging device 104, and a base unit 106.

The mobile device 102 may be a cellular phone, a tablet, a laptop, or another portable computing device. The mobile device 102 may have a display 103. The display 103 may be a liquid crystal display (LCD), a light-emitting diode display (LED), an organic light emitting diode (OLED), a plasma display, a cathode-ray tube (CRT) display, a digital light processing display (DLPT), a microdisplay, a projection display, or any other display appreciated by one of ordinary skill in the art. The display 103 may display user interfaces, text, images, and/or the like. The interface may allow a user to control the mobile device 102 and one or more components of the system 100. The interface may further allow the user to view information outputted by the system 100. The display 103 may be touchscreen and used to input user commands. The mobile device 102 may have an optical camera **108*a*. The optical camera 108*a* may be located on a front side 110 of the mobile device 102 as shown in FIG. 1. In some embodiments, the optical camera 108*a* may be located on a rear side (not shown) of the mobile device 102. The optical camera 108*a* may have an optical instrument to record static or dynamic images. The optical camera 108*a* may have a lens that focuses reflected light from the body part of a person and an image recording mechanism. The optical camera 108*a* may be integrated to the mobile device 102 as shown in FIG. 1. In some embodiments, the optical camera 108*a* may be a separate hardware having a remote body attachable to the mobile device 102 or the system 100** in general. The attachment may utilize all types of universal serial bus (USB) (e.g., micro USB, USB-C), lighting, and any other conventional connection means. The connection may also be a wireless connection utilizing Bluetooth, Infrared (IR), WiFi, and the like.

The mobile device 102 may be attached to the imaging device 104. The attachment may be an electronic attachment. An output device 112 of the imaging device 104 may be coupled to an input device 114 of the mobile device 102. The attachment may utilize all types of USB, lighting, and any other conventional connection means. The connection may also be a wireless connection utilizing Bluetooth, IR, WiFi, and the like. The imaging device 104 may have an optical camera 108*b*. The optical camera 108*b* may be used in lieu of the optical camera 108*a*. The optical camera 108*b* may have the same or similar components to those of the optical camera 108*a*. In some embodiments, the system 100 may either have the optical camera 108*a* or the optical camera 108*b*. The imaging device 104 may further have a thermal camera 116. The thermal camera 116 may have an optical instrument to record static or dynamic images using infrared radiation in the Long Wave Infrared Range (LWIR) (i.e., 0.000315 inches (in) to 0.000551 in, 8 micrometers (μm) to 14 μm). The thermal camera 116 may have a thermal image sensor and an image recording mechanism. The thermal camera 116 may be integrated to the imaging device 104 as shown in FIG. 1. The thermal camera 116 and the optical camera 108*b* may be stacked on top of each other. The thermal camera 116 and the optical camera 108*b* may have the same appearance and exterior features. The thermal camera 116 and the optical camera 108*b* may be vertical to each other as shown in FIG. 1. In some embodiments, the thermal camera 116 and the optical camera 108*b* may be horizontal or diagonal to each other. In some embodiments, the thermal camera 116 may be a separate hardware having a remote body attachable to the imaging device 104 or the system 100 in general. The attachment may utilize all types of USB, lighting, and any other conventional connection means. The connection may also be a wireless connection utilizing Bluetooth, IR, WiFi, and the like. In some embodiments, the thermal camera 116 may be integrated to the mobile device 102.

The mobile device 102 and the imaging device 104 may be mechanically attached to the base unit 106. The base unit 106 may be made of metal, plastic, wood, and/or the like. The base unit 106 may be a unitary construction or composed of several parts coupled together using any known fastening technique (e.g., press-fit, screws, adhesives). The base unit 106 may be shaped and sized to be portable. The base unit 106 may be configured to have a substantially flat bottom surface 117. The substantially flat bottom surface 117 may allow the base unit 106 to rest on a surface. Preferably, the surface may be flat and smooth. The base unit 106 may have filleted edges. The filleted edges may be user friendly and allow the base unit 106 to be held with ease.

The base unit 106 may have a body portion 118 and a device portion 120. The body portion 118 and the device portion 120 may be connected with an extendable portion 122 situated in between the body portion 118 and the device portion 120. The extendable portion 122 may be attached to the body portion 118 and the device portion 120 via a sliding rail mechanism. The body portion 118 and the device portion 120 may be moved away from each other about the extendable portion 122 to extend the base unit 106. In some embodiments, the extendable portion 122 may be one or more separate attachments each having different lengths. The user may select an attachment based on a desired extension length. The desired extension length may depend on the user's size (e.g., height, length of limbs, feet size). The extension may allow the user to adhere to an image capture perimeter of the imaging device 104. For example, the imaging device 104 may require the images of the body parts to be inspected to fit within a virtual template having predetermined dimensions.

The body portion 118 may have a support rest 124 extending therefrom. The support rest 124 may be configured to receive and support the user's legs, ankles, or feet. The support rest 124 may elevate the supported body parts from the body portion 118. In some embodiments, the elevation of the support rest 124 from the body portion 118 may be adjustable. The support rest 124 may have two resting surfaces 126*a,b*. The supported body parts may directly contact the resting surfaces 126*a,b*. The resting surfaces 126*a,b* may each have a curvature shaped and sized to accommodate the supported body parts while complementing the natural shape of the supported body parts.

The device portion 120 may have an imaging connector 128. The imaging connector 128 may be configured to be attached to the imaging device 104. The imaging connector 128 may hold the imaging device 104 in place relative to the support rest 124. This may allow the imaging device 104 to produce better quality images of the body parts due to being still during image capture. The imaging device 104 may be removably attached to the imaging connector 128. Any known non-permanent fastening techniques may be utilized to attach the imaging device 104 to the imaging connector 128 (e.g., insert, mounting clips, hooks, screws). The imaging connector 128 may be further configured to be attached to the mobile device 102. The mobile device 102 may be removably attached to the imaging connector 128. Any known non-permanent fastening techniques may be utilized to attach the mobile device 102 to the imaging connector 128 (e.g., insert, mounting clips, hooks, screws). The imaging connector 128 may be pivotally attached to the device portion 120 or have a pivoting body relative to the device portion 120. The pivotability of the imaging connector 128 may allow the mobile device 102 and the imaging device 104 to be angled as desired. The imaging connector 128 may elevate the mobile device 102 and/or the imaging device 104 from the device portion 120. The elevation of the mobile device 102 and the imaging device 104 from the device portion 120 may each be adjusted, either simultaneously or independently.

Figure 2:
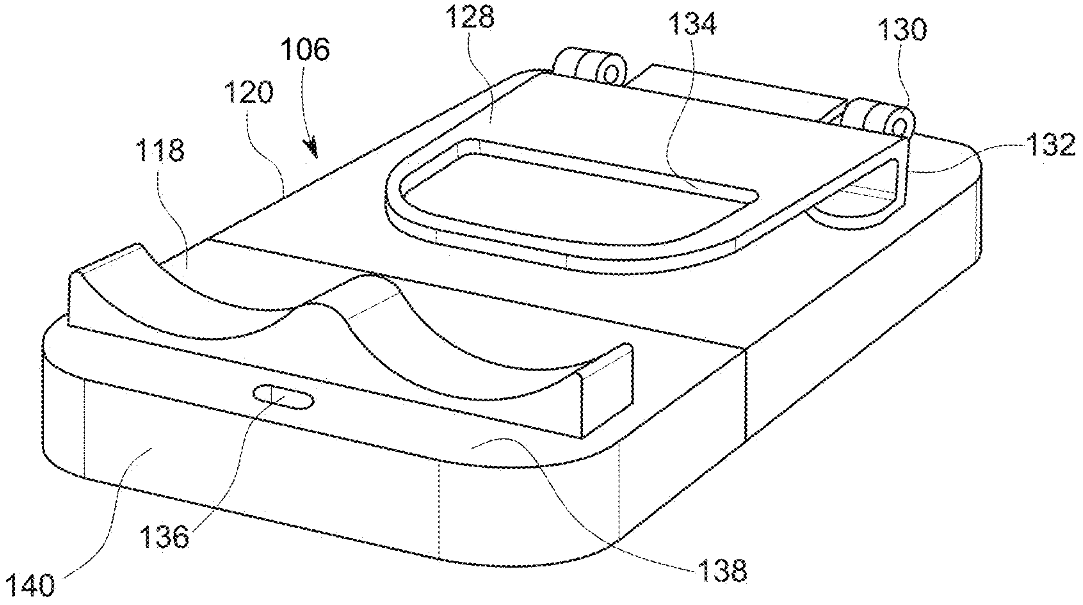
FIG. 2 illustrates a perspective view of a base unit of the system of FIG. 1 in a non-extended position and an imaging connector of the base unit in a closed position according to an aspect of the present disclosure.

FIG. 2 illustrates a perspective view of the base unit 106 in a non-extended position and the imaging connector 128 in a closed position according to an aspect of the present disclosure. The imaging connector 128 may fold into the closed position when the system 100 is not being used but rather being stored or transported. The mobile device 102 and the imaging device 104 may have to be removed from the imaging connector 128 prior to bringing the imaging connector 128 to the closed position. The imaging connector 128 may be pivoted from a pivot joint 130 attaching the imaging connector 128 to an imaging connector base 132. In some embodiments, the pivot joint 130 may attach the imaging connector 128 directly to the base unit 106. In the closed position, the imaging connector 128 may be substantially parallel to the base unit 106. The imaging connector 128 may have an opening 134. The opening 134 may be shaped and sized to allow a user to grip the imaging connector 128 with one or more fingers to traverse the imaging connector 128 between the open position and the closed position. In some embodiments, the opening 134 may be replaced with a protrusion such as a handle or a ring attachment.

The body portion 118 and the device portion 120 may be flush in the non-extended position. The body portion 118 may have a cavity 136. The cavity 136 may be located on a top surface 138 of the body portion 118. The cavity 136 may be near a proximal end 140 if the body portion 118, the proximal end 140 being away from the device portion 120. The cavity 136 may allow the user to grip the body portion with one or more fingers to traverse the base unit 106 between the extended position and the non-extended position. The device portion 120 may also have a cavity (not shown) mirroring the cavity 136. The user may traverse the base unit 106 between the extended position and the non-extended position from the body portion 118, the device portion 120, or both. In some embodiments, the cavity 136 may be replaced with a protrusion.

Figure 3:
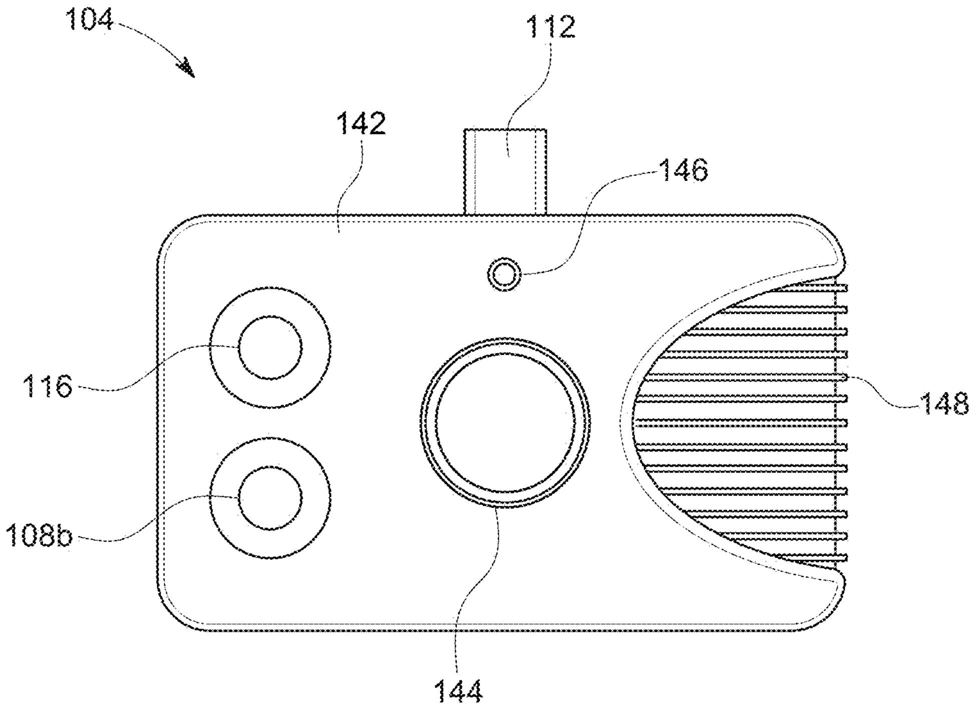
FIG. 3 illustrates a front isolated view of an imaging device of the system of FIG. 1 according to an aspect of the present disclosure.

FIG. 3 illustrates a front isolated view of the imaging device 104 of the system 100 according to an aspect of the present disclosure. The imaging device 104 may have components attached together by a casing 142. The components may include the optical camera 108*b*, the thermal camera 116, the output device 112, an on/off switch 144, a power indicator light 146, a grip 148, and a charging port (not shown). The imaging device 104 may have a battery housed within the casing 142. The battery may be charged via the charging port. The charging port may receive all types of USB, lighting, and any other conventional power cords. In some embodiments, the imaging device 104 may use disposable batteries (e.g., AA, AAA). The power indicator light 146 may indicate whether the imaging device 104 is on, charged, charging, and/or needs charging. The power indicator light 146 may blink and/or emit a specific colored light associated with a power state. The power indicator light 146 may be a light emitting diode (LED). The on/off switch 144 may be used to power on and off the imaging device 104. In some embodiments, the on/off switch 144 may also be used to capture images via the optical camera 108*b* and/or the thermal camera 116. The on/off switch 144 may receive a plurality of inputs by a variety of ways of activating the on/off switch 144 (e.g., pressing a certain number of times, pressing and holding, pressing all the way in, sliding). The grip 148 may be a rough surface on the casing 142. The grip 148 may extend to a plurality of sides of the casing 142. The grip 148 may allow the user to comfortably hold the imaging device 104 without covering the optical camera 108*b* or the thermal camera 116, thereby mitigating drops and creating unwanted fingerprint marks on the optical camera 108*b* and the thermal camera 116.

Figure 4:
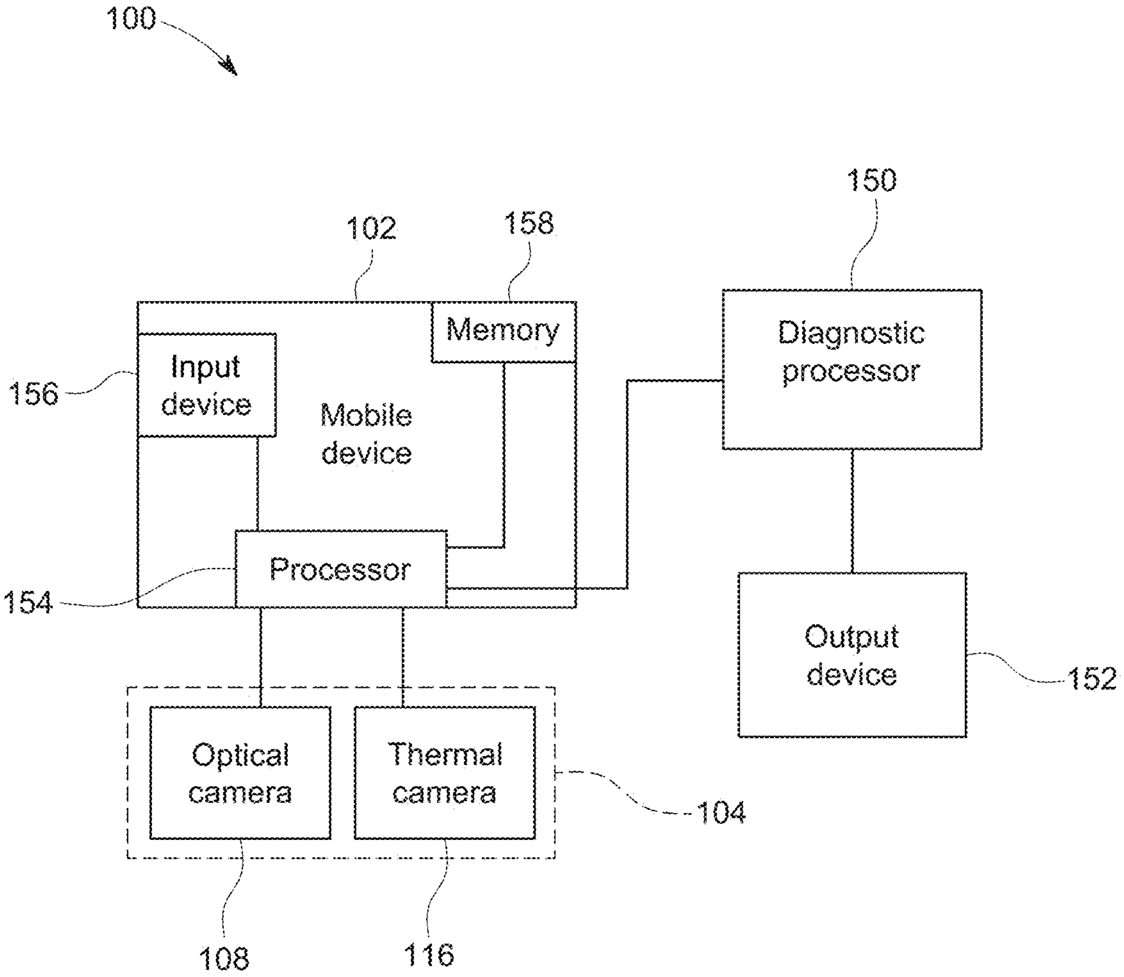
FIG. 4 is a block diagram illustrating various components of the system of FIG. 1 according to an aspect of the present disclosure.

FIG. 4 is a block diagram illustrating various components of the system 100 according to an aspect of the present disclosure. The system 100 may include the mobile device 102, the imaging device 104, a diagnostic processor 150, and an output device 152. The mobile device 102 may have a processor 154. The processor 154 may be configured to execute machine-readable instructions. In some embodiments, there may be a plurality of processors 154. The processor 154 may be a microprocessor or a microcontroller by example. The processor 154 may be programmed to control the thermal camera and/or the optical camera to detect the thermal images and/or the optical images based on the user's input.

The user input may be received via an input device 156. The input device 156 may be integrated to the mobile device 102. The input device 156 may receive visual, auditory, and/or touch input. For example, the input device 156 may be a camera, a microphone, a touchscreen, a button, or a remote. The input device 156 may be integrated with the display 103 of the mobile device 102. The input device 156 may receive biometric information, the user's voice, and/or the user's touch input with one or more fingers. The input may be a request to begin image capture.

In some embodiments, the mobile device 102 may be controlled automatically using an algorithm stored in a memory 158. The memory 158 may be a random-access memory (RAM), a disk, a flash memory, optical disk drives, hybrid memory, or any other storage medium that can store data. The memory 158 may store program code that are executable by the processor 154. The memory 158 may store data in an encrypted or any other suitable secure form. The mobile device 102 may be controlled to begin detecting images as soon as a known or recognized image is in the field of view of the optical camera 108 and/or the thermal camera 116. After images are detected, the mobile processor 154 may transmit the images to the diagnostic processor 150.

The diagnostic processor 150 may have diagnostic, monitoring, and prognostic capabilities. The diagnostic processor 150 may be part of a remote computer or part of a remote server. The diagnostic processor 150 may communicate with the mobile device 102 wirelessly or by a wired connection. The wireless communication may be through internet, WiFi, Bluetooth, IR, and the like. In some embodiments, some or all of the aforementioned communication methods may be available for selection of the user based on preference or suitability (e.g., signal travel distance, signal availability, signal interference, signal travel speed). The wired communication may use all types of USB, lighting, and the like. In some embodiments, the diagnostic processor 150 may be integrated to the mobile device 102. The diagnostic processor 150 may be implemented on a plurality of computers connected in a network or a plurality of virtual machines in a could infrastructure. The remote computer or the remote server may store, analyze, and compare the transmitted images. The remote computer or the remote server may store data including optical and thermal images, files, and user account information. The diagnostic processor 150 may identify an outline of the inspected body part and the reference body part, evaluate temperature differences, and determine that a functional disorder or inflammation of the inspected body part has occurred among other things. The diagnostic processor 150 may use filtering technologies and advanced statistical models to perform some or all of its functions. In some embodiments, machine learning and artificial intelligence may be utilized to perform some or all of its functions. The diagnostic processor 150 may send feedback to the mobile device 102 and/or the output device 152.

The output device 152 may configured to output status data of the imaging device 104. The status data may include optical and thermal images detected by the imaging device 104 and/or data outputted by the diagnostic processor 150 upon conducting an analysis of the optical and thermal images. The output device 152 may present the status data visually or auditorily. The output device 152 may be a display (e.g., touchscreen), a speaker, or the like. The display may be a liquid crystal display (LCD), a light-emitting diode display (LED), an organic light emitting diode (OLED), a plasma display, a cathode-ray tube (CRT) display, a digital light processing display (DLPT), a micro-display, a projection display, or any other display appreciated by one of ordinary skill in the art. The display may display user interfaces, text, images, and/or the like. In some embodiments, the output device 152 may be integrated with the mobile device 102 or the imaging device 104. The output device 152 may communicate with the diagnostic processor 150 wirelessly or by a wired connection. The wireless communication may be through internet, WiFi, Bluetooth, IR, and the like. In some embodiments, some or all of the aforementioned communication methods may be available for selection of the user based on preference or suitability (e.g., signal travel distance, signal availability, signal interference, signal travel speed). The wired communication may use all types of USB, lighting, and the like.

The status data may also be directly transmitted to a healthcare professional who is assigned to monitor the feet or overall health of the user. The transmission may be conducted via email, phone, text message, software notification, or another means of data transfer. The status data may be encrypted during transmission and decrypted once received. When the user and/or his/her assigned healthcare professional receives the feedback about the health state of the feet, they can determine an appropriate course of treatment.

Figure 5A:
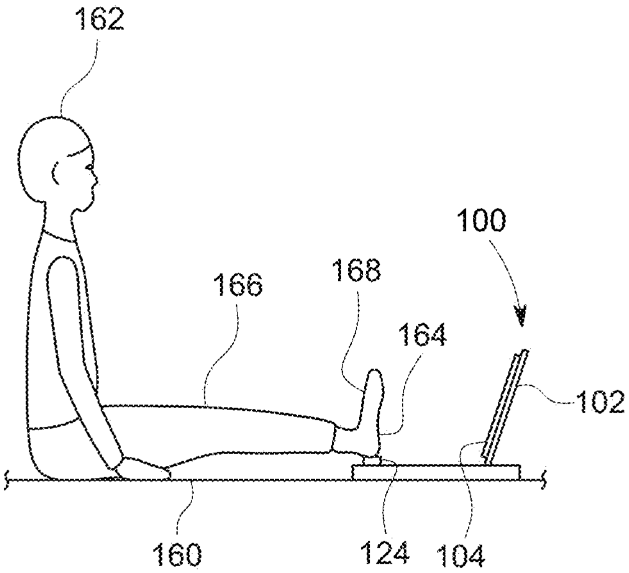
FIG. 5A illustrates a method of using the system of FIG. 1 according to an aspect of the present disclosure.

FIG. 5A illustrates a method of using the system 100 according to an aspect of the present disclosure. The system 100 may be placed on a flat surface 160. The user may be a patient 162. The patient 162 may self-inspect his/her feet, ankles, and/or legs. The patient 162 may place and rest his/her heels 164 on the support rest 124. This may require the patient to be in a seated position on the flat surface 160 or another suitable surface in proximity of the system 100. The legs 166 of the patient may be extended such that there is minimal bending from the knees and the legs 166 are substantially parallel to the flat surface 160. The mobile device 102 and the imaging device 104 may be facing the patient 162 such that the optical camera 108 and the thermal camera 116 are facing the feet 168 of the patient. The patient 162 may lie down if desired or necessary.

Figure 5B:
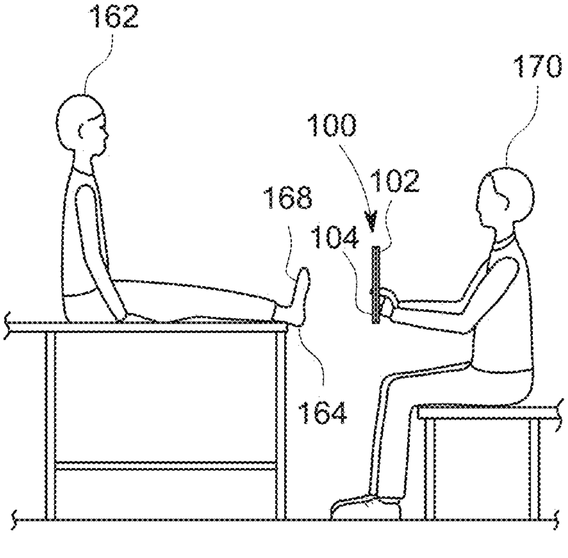
FIG. 5B illustrates a method of using the system of FIG. 1 according to an aspect of the present disclosure.

FIG. 5B illustrates a method of using the system 100 according to an aspect of the present disclosure. The users may be the patient 162 and an aide 170. A healthcare professional, a guardian, a friend, a parent, or a caregiver may serve as the aide 170. The aide 170 may hold the mobile device 102 and the imaging device 104. The patient 162 may be in the same position as in FIG. 5A except the heels 164 may not be directly resting on a surface. The aide 170 may position himself/herself to hold the imaging device 104 such that the optical camera 108 and the thermal camera 116 are facing the feet 168 of the patient 162 and within their scope. The aide 170 may then use the output device 152, which may be the mobile device 102 or the imaging device 104, to receive feedback of the analysis.

Figure 6:
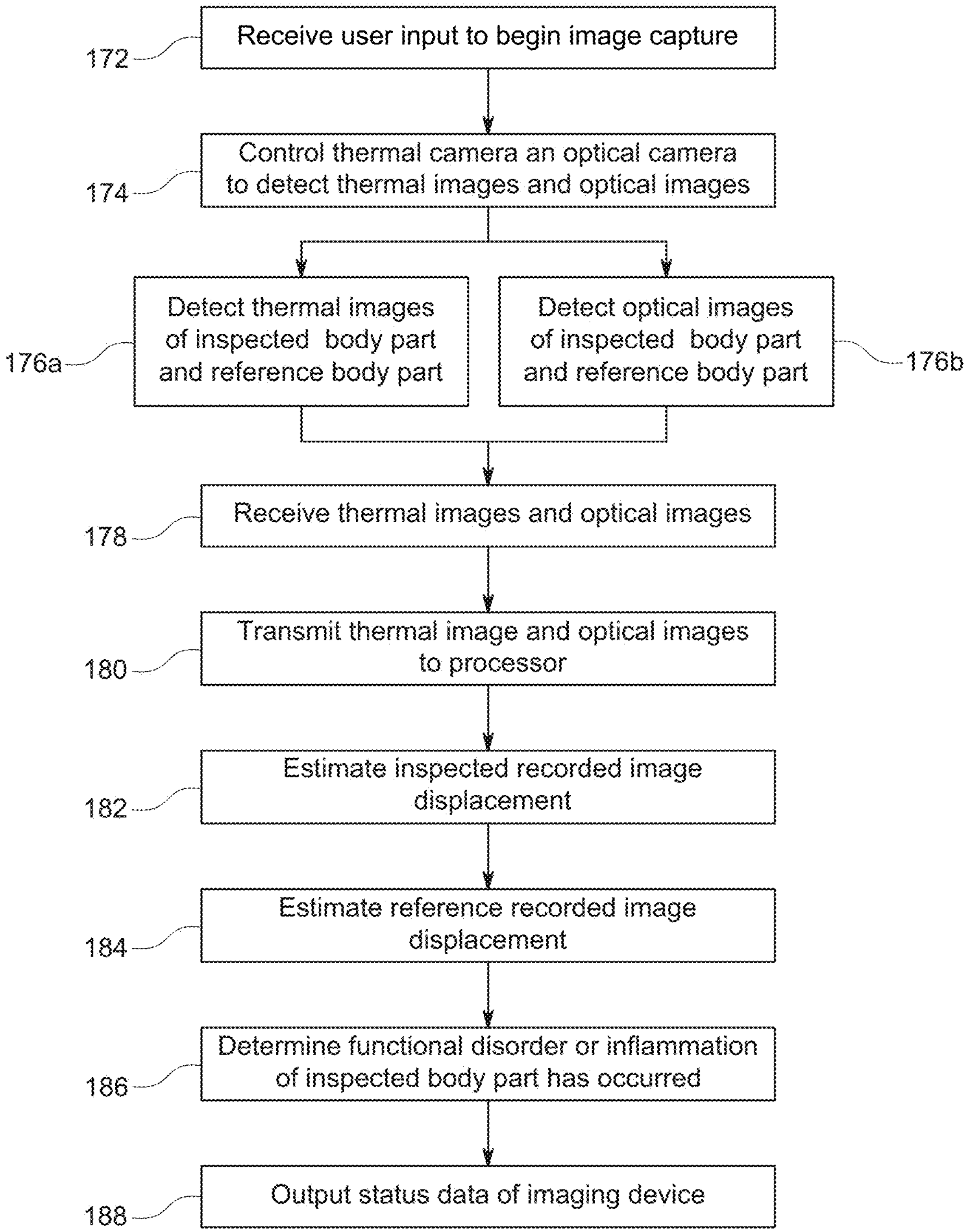
FIG. 6 is a flowchart illustrating a method for identifying a health disorder based on a temperature asymmetry estimation according to an aspect of the present disclosure.

FIG. 6 is a flowchart illustrating a method for identifying a health disorder based on a temperature asymmetry estimation according to an aspect of the present disclosure. The method may begin with receiving a user input to begin image capture in block 172. The user input may be received via the input device 156. The input device 156 may be integrated with the mobile device 102. The received input may activate the optical camera 108 and the thermal camera 116. The user may have to register or login to a user account through the input device 156 prior to inputting the command to begin image capture. The method may continue with block 174.

In block 174, the optical camera 108 and the thermal camera 116 may be controlled via the mobile processor 154 to detect optical images and thermal images of an inspected body part and a reference body part. The control commands may be inputted via the input device 156. In some embodiments, the mobile processor 154 may autonomously control the optical camera 108 and the thermal camera 116 to be begin detecting the optical images and the thermal images upon detecting that the inspected body part and the reference body part are in the correct location relative to the optical camera 108 and the thermal camera 116. The method may continue with blocks 176*a,b* simultaneously or one after another.

In block 176*a*, a thermal image of an inspected body part and a thermal image of a reference body part may be detected by the thermal camera 116. In block 176*b*, the optical image of the inspected body part and the optical image of the reference body part may be detected by the optical camera 108. In some embodiments the thermal images and the optical images may be detected simultaneously. For example, the thermal images and the optical images may be detected at the same time, within 0.1 seconds of each other, within 0.5 seconds of each other, within 1 second of each other, or the like. In some embodiments, the thermal images and the optical images may be detected one after another. One of the optical images and the thermal images may be detected seconds or minutes apart from the other of the optical images and the thermal images. The inspected body part and the reference body part must be approximately in the same position during the detection of the optical images and the thermal images. The optical image and the thermal image of the inspected body part may be detected simultaneously, before, or after the optical image and the thermal image of the reference body part. The method may continue with block 178.

In block 178, the mobile device 102 may receive the detected thermal images and the optical images. The output device 112 of the imaging device 104 may transmit the thermal images and the optical images to the input device 114 of the mobile device 102. The attachment may utilize all types of USB, lighting, and any other conventional connection means. The connection may also be a wireless connection utilizing Bluetooth, IR, WiFi, and the like. In some embodiments, the optical camera 108 and/or the thermal camera 116 may be integrated to the mobile device 102. The transmission may be conducted within the mobile device 102 in such embodiments. The mobile device 102 may store the thermal images and the optical images in the memory 158 and/or on the cloud. The mobile device 102 may also transmit the thermal images and the optical images to the diagnostic processor 150 in block 180 without storing the thermal images and the optical images.

In block 180, the mobile device 102 may transmit the thermal images and the optical images to the diagnostic processor 150. The diagnostic processor 150 may be part of a remote computer or part of a remote server. The mobile device 102 may communicate with the diagnostic processor 150 wirelessly or by a wired connection. The wireless communication may be through internet, WiFi, Bluetooth, IR, and the like. The wired communication may use all types of USB, lighting, and the like. In some embodiments, the diagnostic processor 150 may be integrated to the mobile device 102. The transmission may be conducted within the mobile device 102 in such embodiments. The thermal images and the optical images may be stored in the remote server or the remote computer. The diagnostic processor 150 may retrieve the stored thermal images and the optical images to conduct analysis. The method may continue with block 182.

In block 182, the diagnostic processor 150 may estimate an image displacement of the recorded images of the inspected body part. The image displacement may be based on the optical images and the thermal images of the inspected body part. In block 184, the diagnostic processor 150 may estimate an image displacement of the recorded images of the reference body part. The image displacement may be based on the optical images and the thermal images of the reference body part. The steps of blocks 182, 184 may be performed simultaneously or sequentially without any particular order.

While estimating image displacement, there may be keypoints located in both the thermal images and the optical images. Preferably, the keypoints may be clearly visible both in the thermal images and the optical images (e.g. sharp edges). Also preferably, the keypoints may represent the same object or part thereof. By solving the optimization problem in any widely known way (e.g. descent gradient, genetic algorithm) an offset may be obtained by adjusting the thermal images and the optical images in such a way that the total nonconformity error between corresponding pairs of keypoints become minimal. The nonconformity error may be calculated as an error function representing the distance between corresponding pairs of keypoints in any known or other method (e.g., Root Mean Square Error).

A template of the inspected body part may be localized based on the inspected body part outline in the thermal image and the optical image of the inspected body part. An affine transformation capable of transforming the reference body part image to correspond to the inspected body part outline in the thermal image and the optical image may be estimated. Transformation parameters (e.g., scale, rotation, translation, mirror, shear) may be estimated by solving the optimization problem in any known way (e.g. descent gradient, genetic algorithm). Body part templates compliancy may be estimated in any known way of vector line correspondence to line or edge represented in image, such as edge detection. Deformable templates matching may be used to identify the outline of inspected and reference body parts outlines in the thermal image and the optical image.

The inspected body part template may be fine-tuned based on the inspected body part outline in the thermal image and the optical image of the inspected body part. During the fine-tuning process, the points of the inspected body part template transformed with affine transformation may be matched with the body part outline line or edge to achieve an optimal fit. However, the anatomical body part shape may be preserved by using accumulated reciprocal positions of corresponding points in a previously analyzed body part shape. Thus, the body part shape may be obtained by fitting the body part shape on the thermal image and the optical image.

A template of the reference body part may be localized based on the reference body part outline in the thermal image and the optical image of the reference body part. An affine transformation capable of transforming the base body part image to correspond to the reference body part outline in the thermal image and the optical image may be estimated. Transformation parameters (e.g., scale, rotation, translation, mirror, shear) may be estimated by solving the optimization problem in any known way (e.g. descent gradient, genetic algorithm). Body part templates compliancy may be estimated in any known way of vector line correspondence to line or edge represented in image, such as edge detection.

The reference body part template may be fine-tuned based on the reference body part outline in the thermal image and the optical image of the reference body part. During the fine-tuning process, the points of reference body part template transformed with affine transformation may be matched with the body part outline line or edge to achieve an optimal fit. However, an anatomical body part shape may be preserved by using accumulated reciprocal positions of corresponding points in previously analyzed body part shapes. Thus, the body part shape may be obtained by fitting the body part shape on the thermal image and the optical image.

Sets of points of interest for the inspected body part and the reference body part may be estimated based on appropriate body part templates. The positions of points of interest may be estimated by applying affine and non-affine transformations in succession to the base set of points of interest for each body part. Non-affine transformation coefficients may be estimated according to the body part template points of the appropriate body part. Additional points laid inside the body part shape polygon may also be used for better transformation preparation.

Temperature maps for the inspected body part and the reference body part may be estimated according the appropriate set of points of interest. Each value of the temperature maps may be estimated by generalizing temperature values situated near the position of points of interest in the thermal image of the appropriate body part. Any known type of temperature values generalization may be used (e.g. mean, median, weighted mean). A temperature disparity map may be estimated. The estimation may be performed by subtracting the temperature values in the temperature map of the reference body part from the appropriate temperature values in the temperature map of the inspected body part.

In block 186, an occurrence of a functional disorder or inflammation of the inspected body part may be determined by the diagnostic processor 150. A composition of inflammation or functional disorder regions may be performed by analyzing the temperature disparity map in order to find the local areas containing temperature disparity values higher than the medically based threshold. Candidate inflammation or functional disorder regions may be composed of the nearby points of the temperature disparity map exceeding a medically based threshold. The threshold may be found in medical literature, set by a researcher or a doctor, or found via any other method. A descriptive feature vector may be created for each candidate inflammation or functional disorder region composed of estimations of generalized values of points, interposition, temperatures, or any combination thereof.

An analysis of inflammation or functional disorder regions may be performed by examining the feature vectors. During this process, non-confident inflammation or functional disorder regions may be rejected in order to clear the list against accidentally marked non-inflammable regions (e.g. the area deemed too small, having a relatively small temperature excess). For better compliancy, any historically accumulated data may be used to perform this task. Any type of classificatory or machine learning functional step may be used to perform this task (e.g. a support vector machine, an artificial neural network).

Each inspected body part may have a threshold for the temperature differences that signal an inflammation or a functional disorder. The temperature differences may be obtained by comparing the differences in thermal images of the inspected and reference body parts. If an unpaired body part is inspected, the comparison may be made between the inspected body part and an area adjacent to the unpaired inspected body part. For example, if an area of the abdomen is inspected, then an adjacent area on the abdomen may be referenced for the comparison). The same inspected body part may be used as a reference or contralateral body part when data from a different and previously detected thermal image is used. Temperature differences that surpass the threshold value may indicate inflammation of the body part. Further, early onset of inflammation or another other functional disorder may be suspected.

In block 188, the status data of the imaging device 104 may be outputted by the output device 152. The output device 152 may present the status data visually or auditorily. The output device 152 may receive the status data from the diagnostic processor 150 wirelessly or by a wired connection. The wireless communication may be through internet, WiFi, Bluetooth, IR, and the like. The wired communication may use all types of USB, lighting, and the like. By reviewing the status data, the user is informed about his/her health or his/her patient's health. If the temperature differences are below the threshold value, the user is informed that the signs for the functional disorder or inflammation of the inspected body parts were not detected by the system 100. If the temperature differences surpass the threshold value, the user is informed about the signs for the early onset of inflammation or other functional disorder and is advised to consult a health professional for further examination.

Where used throughout the specification and the claims, "at least one of A or B" includes "A" only, "B" only, or "A and B." Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

The invention claimed is:

1. A system for identifying health conditions based on temperature differences, the system comprising:

an imaging device having a casing enclosing an optical camera configured to detect optical image data corresponding to an inspected body part and a reference body part and a thermal camera configured to detect thermal image data corresponding to the inspected body part and the reference body part, wherein the optical camera and thermal camera are mounted at a fixed offset relative to each other;

an input device inside the casing coupled to a switch; and a processor coupled to the imaging device and configured to, in response to the actuation of the switch:

receive or determine temperature values in a plurality of locations for each of the inspected and reference body parts based on the optical image data and the thermal image data, determine temperature disparity values between the temperatures at locations corresponding to the inspected body part and the reference body part, compare the temperature disparity values to a medically based threshold, and determine whether the temperature disparity values indicate a condition of the inspected body part at or near one or more of the locations based on whether or not a temperature disparity value greater than the medically based threshold is detected at the locations corresponding to the inspected body part.

2. The system of claim 1 wherein the condition is a functional disorder or inflammation of the inspected body part.

3. The system of claim 1 wherein the condition is a normal condition of the inspected body part.

4. The system of claim 1 further comprising an output device coupled to the processor for reporting the condition of the inspected body part.

5. The system of claim 1 wherein the reference body part is an area adjacent to the inspected body part.

6. The system of claim 1, wherein the functional disorder or inflammation is an early diagnosis of a diabetic-related condition.

7. The system of claim 1, wherein the inspected body part is a foot and the reference body part is a contralateral foot.

8. The system of claim 1, wherein the inspected body part is a foot and the reference body part is the same foot.

9. The system of claim 1, wherein the inspected body part is located in the abdomen.

10. The system of claim 1, further comprising an output device coupled to the processor and configured to output data corresponding to the identification of the condition of the inspected body part.

11. The system of claim 1, wherein the processor is further configured to estimate a temperature map of the inspected body part and estimate a temperature map of the reference body part to determine the temperature values at the corresponding locations for each of the inspected body part and the second body part, and to estimate a temperature disparity map between the first body part and the second body part to determine the temperature disparity values.

12. The system of claim 1, wherein the processor is further configured to identify the condition of the inspected by creating a descriptive feature vector for each of a plurality of body regions.

13. The system of claim 12, wherein the processor is further configured to identify a condition of the inspected body part by rejecting at least one non-confident body region from a plurality of candidate regions based on the descriptive feature vector.

14. The system of claim 13, wherein the processor is further configured to reject the at least one non-confident region using at least one of a classificatory tool or a machine learning tool.

15. The system of claim 1, wherein:

the optical image data and the thermal image data corresponding to the first body part are detected at a first time; and the optical image data and the thermal image data corresponding to the second body part are detected at a second time that is different than the first time.

16. The system of claim 1, further comprising a base having a support rest configured to support the inspected body part and the reference body part, the base being further configured to be mechanically coupled to the imaging device.

17. The system of claim 16, wherein the base includes a body portion having the support rest, a device portion having a connector configured to be mechanically coupled to the imaging device, and an extendable portion between the body portion and the device portion and configured to at least one of extend or contract to adjust a distance between the support rest and the connector.

18. The system of claim 1, further comprising a mobile device electrically coupled to the processor and having a display configured to output data corresponding to the identification of the condition of the inspected body part.

19. A system for early identification of a medical condition based on temperature estimation, the system comprising:

an imaging device having a casing enclosing an optical camera configured to detect optical image data corresponding to an inspected region of a body part and a reference region of a body part and a thermal camera configured to detect thermal image data corresponding to the inspected and reference regions, wherein the optical camera and thermal camera are mounted at a fixed offset relative to each other;

an input device inside the casing coupled to a switch;

a base having a support rest configured to support a body part and having a connector configured to be mechanically coupled to the optical camera and the thermal camera; and a processor coupled to the imaging device and configured to in response to the actuation of the switch:

receive or determine an estimated temperature disparity map between the inspected region and the reference region based on the optical image data and the thermal image data, compare the temperature disparity map to a medically based threshold, and identify a medical condition in response to the temperature disparity map.

20. A portable device for identifying a health condition based on temperature asymmetry estimation, the system comprising:

a casing enclosing an optical camera, a thermal camera, a battery, a switch, an input device coupled to the switch, and an output device;

the casing having an exterior surface with a grip to facilitate handling of the portable device;

the optical camera configured to detect optical image data corresponding to an inspected body part and a reference body part;

the thermal camera configured to detect thermal image data corresponding to the inspected body part and the reference body part, wherein the optical camera and thermal camera are mounted at a fixed offset relative to each other; and a processor coupled to the imaging device and configured to, in response to a signal from the switch:

receive or determine temperature values at corresponding locations for each of the inspected body part and the reference body part based on the optical image data and the thermal image data, determine temperature disparity values between the inspected body part and the reference body part at each of the locations, compare the temperature disparity values to a medically based threshold, and identify that a normal or abnormal medical condition of the inspected body part exists at or near one or more of the locations in response to a temperature disparity value with respect to a medically based threshold at the location, and communicate to the output device information related to the identification of a normal or abnormal medical condition, thereby enabling the imaging device to display the information.

* * * * *